United States Patent [19]
Spaulding et al.

[11] Patent Number: 5,637,477
[45] Date of Patent: Jun. 10, 1997

[54] RECOMBINANT PROTEIN PRODUCTION AND INSECT CELL CULTURE AND PROCESS

[75] Inventors: Glenn F. Spaulding, Houston; Thomas J. Goodwin, Friendswood, both of Tex.; Kim C. O'Connor, New Orleans, La.; Karen M. Francis, Aiken, S.C.; Angela D. Andrews, Pensacola, Fla.; Tacey L. Prewett, Friendswood, Tex.

[73] Assignee: The United States of America as respresented by the Administrator of the National Aeronautics and Space Administration, Washington, D.C.

[21] Appl. No.: 291,791

[22] Filed: Aug. 16, 1994

Related U.S. Application Data

[63] Continuation-in-part of Ser. No. 62,856, May 14, 1993, abandoned.

[51] Int. Cl.$^6$ .............................. C12P 21/00; C12N 5/10
[52] U.S. Cl. ................. 435/69.1; 435/320.1; 435/172.3; 435/69.2; 435/69.3; 435/69.4; 435/69.5; 435/69.51; 435/69.52; 435/69.6; 435/69.7; 536/23.1; 935/33; 935/34; 935/60; 935/66; 935/70
[58] Field of Search ........................... 435/320.1, 240.2, 435/172.3, 69.1, 69.2, 69.3, 69.4, 69.5, 69.51, 69.52, 69.6, 69.7; 536/23.1; 935/33, 34, 60, 66, 70

[56] References Cited

U.S. PATENT DOCUMENTS

| | | | |
|---|---|---|---|
| 4,804,628 | 2/1989 | Cracauer et al. | 435/240.242 |
| 4,988,623 | 1/1991 | Schwarz et al. | 435/297.3 |
| 5,024,947 | 6/1991 | Inlow et al. | 435/240.31 |
| 5,077,214 | 12/1991 | Guarino et al. | 435/240.2 |
| 5,081,035 | 1/1992 | Halberstadt et al. | 435/297.4 |
| 5,122,469 | 6/1992 | Mather et al. | 435/240.2 |
| 5,153,131 | 10/1992 | Wolf et al. | 435/240.24 |

OTHER PUBLICATIONS

"Spin Filter Perfusion System for High Density Cell Culture: Production of Recombinant Urinary Type Plasminogen Activator in CHO Cells," Avegerinos, G.C., Drapeau, D., Socolow, J.S., Mao, J.-I., Hsiao, K., and Broeze, R.J., *Biotechnology*, 8, 54–58 (1990).
"Three–Dimensional Growth and Differentiation of Ovarian Tumor Cell Line in High Aspect Rotating–Wall Vessel: Morphologic and Embryologic Considerations," Becker, J.L., Prewett, T.L., Spaulding, G.F., and Goodwin, T.J., *J. Cell Biochem.*, 51, 283–289 (1993).
"Protein Synthesis Requires Cell–Surface Contact while Nuclear Events Respond to Cell Chape in Anchorage–Dependent Fibroblasts," Ben–Ze'ev, A., Farmer, S.R., and Penman, S. *Cell.*, 21, 365–372 (1980).
Cavegn, C., Young, J., Bertrand, M., and Bernard, A.R., "Animal Cell Technology: Products of Today, Prospects for Tomorrow," Spier, R.E., Griffiths, J.B., and Berthold, W., Eds., *European Society for Animal Cell Technology* (Butterworth–Heinemann, Oxford, 1994, pp. 43–49).
"Microscopic Visualization of Insect Cell–Bubble Interactions II: The Bubble Film and Bubble Rupture," Chalmers, J.J. and Bavarian, F. *Biotechnol. Prog.*, 7, 151–158 (1991).
"Modification of Radiotherapy by Radiosensitizers and Cancer Chemotherapy Agents. I., Radiosensitizers," Coleman, C.N. *Semin. Oncol.*, 16, 169–175 (1989).
"Polybrene–Mediated Transfection of Cultured Lepidopteran Cells: Induction of a Drosophila Heat Shock Promoter," Helgen, J.C. and Fallon, A.M., *In Vitro Cell Dev. Biol.*, 26, 731–736 (1990).
Hugler, W., "Protein Expression of Sf9 Cells Under Stress and Simulated Microgravity," Thesis, Tulane University (1994), Title page, p. 11, pp. 29–35, 59, and 63–65.
"Use of Early Baculovirus Promoters for Continuous Expression and Efficient Processing of Foreign Gene Products in Stably Transformed Lepidopteran Cells," Jarvis, D.L., Fleming J.–A.G.W., Kovacs, G.R., Summers, M.D., and Guarino, L.A., *Biotechnology*, 8, 950–955 (1990).
"Culture of Insect Cells in a Helical Ribbon Impeller Bioreactor," Kamen, A.A., Tom, R.L., Caron, A.W., Chavarie, C., Massie, B., and Archambault, J., *Biotechnol. Bioeng.*, 38, 619–628 (1991).
"Growth of Baculovirus–Infected Insect Cells in Microcapsules to a High Cell and Virus Density," King, G.A., Daugulis, A.J., Faulkner, P., Bayly, D., and Goosen, M.F.A., *Biotechnol. Lett.*, 10, 683 687 (1988).
"Effects of Oxygen on Recombinant Protein Production by Suspension Cultures of *Spodoptera frugiperda* (Sf–9) Insect Cells," Scott, R.I., Blanchard, J.H., and Ferguson, C.H.R., *Enzyme Microb. Technol.*, 14, 798–804 (1992).
"Effects of Oxygen/Glucose/Glutamine Feeding on Insect Cell Baculovirus Protein Expression: A Study on Epoxide Hydrolase Production," Wang, M.Y., Kwong, S., and Bentley, W.E. *Biotechnol. Prog.*, 9, 355–361 (1993).
"Biopharmaceuticals Overcoming Market Hurdles," Thayer, A.M., *C & EN*, Feb. 25, 27–48 (1991).

(List continued on next page.)

*Primary Examiner*—Christopher S. F. Low
*Attorney, Agent, or Firm*—James M. Cate

[57] ABSTRACT

A process has been developed for recombinant production of selected polypeptides using transformed insect cells cultured in a horizontally rotating culture vessel modulated to create low shear conditions. A metabolically transformed insect cell line is produced using the culture procedure regardless of genetic transformation. The recombinant polypeptide can be produced by an alternative process using virally infected or stably transformed insect cells containing a gene encoding the described polypeptide. The insect cells can also be a host for viral production.

11 Claims, 4 Drawing Sheets

OTHER PUBLICATIONS

"Enhanced Myocardial Salvage by Maintenance of Microvascular Patency Following Initial Thrombolysis with Recombinant Tissue Plasminogen Activator," Longridge, D.J., Follenfant, M.J., Maxwell, M.P., Ford, A.J., and Hughes B., *Cardiovasc. Res.*, 24, 697–706 (1990).

"Treatment of the Anemia of Progressive Renal Failure with Recombinant Human Erthropoietin," Eschbach, J.W., Kelly, M.R., Haley, N.R., Abels, R.I., and Adamson, J.W., *N. Engl. J. Med.*, 321, 158–162 (1989).

"Treatment of Sickle Cell Anemia with Hydroxyurea and Erthropoietin," Goldberg, M.A., Brugnara, C., Dover, G.J., Schapira, L., Charache, S., and Bunn, H.F., *N. Engl. J. Med.*, 323, 366–372 (1990).

"Prevalence and Pathologic Features of Sickle Cell Nephropathy and Response to Inhibition of Angiotensin–Converting Enzyme," Falk, R.J., Scheinman, J., Phillips, G., Orringer, E., Johnson, A., and Jennette, J.C., *N. Engl. J. Med.*, 326, 910–915 (1992).

"Ketoconazole an Inhibitor of the Cytochrome P–450 Dependent Testosterone Biosynthesis," Bossche, H.V., Lauwers W., Willemsens, G., Cools, W., *Prog. Clin. Biol. Res.*, 185A, 187–196 (1985).

"Expression Systems for Heterologous Protein Production," Marino, M.H., *BioPharm*, Jul./Aug., 18–33 (1989).

"The Expression of Recombinant DNA Products in Mammalian Cells," Bebbington, C. and Hentschel, C., *Trends Biotechnol.*, 3, 314–317 (1985).

"Concentrating Mammalian Cells I. Large–Scale Animal Cell Culture," Merten, O.W., *Trends Biotechnol.*, 5, 230–238 (1987).

"Industrial–Scale Mammalian Cell Culture, Part 1: Bioreactor Design Considerations," Nelson, K.L., *BioPharm.*, Feb., 42–46 (1988).

"Bubble–Column Design for Growth of Fragile Insect Cells," Tramper, J., Smit, D., Straatman, J., and Vlak, J.M., *Bioprocess Eng.*, 3, 37–41 (1988).

"Manufacturing Steps in Animal Cell–Derived Biopharamaceutical Production," Rhodes, M., *Genetic Engineering News*, 10, Mar., 7 (1990).

"Industrial–Scale Mammalian Cell Culture, Part II: Design and Scale–Up," Nelson, K.L., *BioPharm.*, Mar., 34–50 (1988).

"Agitation Effects on Microcarrier and Suspension CHO Cells," O'Connor, K. C. and Papoutsakis, E. T., *Biotechnol. Tech.*, 6, 323–328 (1992).

"Damage Mechanisms of Suspended Animal Cells in Agitated Bioreactors with and Without Bubble Entrainment," Kunas, K.T. and Papoutsakis, E. T., *Biotechnol. Bioeng.*, 36, 476–483 (1990).

"Hydrodynamic Effects on Cells in Agitated Tissue Culture Reactors," Cherry, R.S. and Papoutsakis, E. T., *Bioprocess Eng.*, 1, 29–41 (1986).

"Hydrodynamic Effects on Animal Cells Grown in Microcarrier Cultures," Croughan, M.S., Hamel, J.F., and Wang, D.I.C., *Biotechnol. Bioeng.*, 29, 130–141 (1987).

"Flow Effects on the Viability and Lysis of Suspended Mammalian Cells," McQueen, A., Meilhoc, E., and Bailey, J.E., *Biotechnol. Letters*, 9, 831–836 (1987).

"Reduced Erythrocyte Deformability Associated with Calcium Accululation," O'Rear, E. A., Udden, M. M., McIntire, L. V., and Lynch E. C., *Biochim. Biophys. Acta*, 691, 274–280 (1982).

"Effect of Flow on Polymorphonuclear Leukocyte/Endothelial Cell Adhesion," Lawrence, M.B., McIntire, L. V., and Eskin, S. G., *Blood*, 70, 1284–1290 (1987).

"Mechanical Effects on Endothelial Cell Morphology: In Vitro Assessment," Ives, C. L., Eskin, S. G., and McIntire, L. V., *In Vitro Cell. Dev. Biol.* 22, 500–507 (1986).

"Tissue Plasminogen Activator Messenger RNA Levels Increase in Cultured Human Endothelial Cells Exposed to Laminar Shear Stress," Diamond, S.L., Sharefkin, J.B., Dieffenbach, C., Frasier–Scott, D., McIntire, L. V., and Eskin, S. G., *J. Cell. Physiol.*, 143, 364–371 (1990).

"Micropipette Aspiration of Cultured Bovine Aortic Endothelial Cells Exposed to Shear Stress," Sato, M., Levesque, M. J., and Nerem, R. M., *Arteriosclerosis*, 7, 276–286 (1987).

"Growth and Death in Overagitated Microcarrier Cell Cultures," Croughan, M.S., Hamel, J.F., and Wang, D. I. C., *Biotechnol. Bioeng.*, 33, 731–744 (1989).

"Shear Sensitivity of Cultured Hybridoma Cells (CRL–8018) Depends on Mode of Growth, Culture Age and Metabolite Concentration," Petersen, J.F., McIntire, L. V., and Papoutsakis, E. T., *J. Biotechnol.*, 7, 229–246 (1988).

"Expression of Human Plasminogen cDNA in a Baculovirus Vector–Infected Insect Cell System," Whitefleet–Smith, J., Rosen, E., McLinden, J., Ploplis, V. A., Fraser, M. J., Tomlinson, J. E., McLean, J. W., and Castellino, F.J., *Arch. Biochem. Biophys.*, 271, 390–399 (1989).

Invited Review "Expression of Eucaryotic Genes in Insect Cell Cultures," Fraser, M. J., *In Vitro Cell. Dev. Biol.*, 25, 225–235 (1989).

Summers, M. D. and Smith, G. E., "A Manual of Methods for Baculovirus Vectors and Insect Cell Culture Procedures," *Texas Agricultural Experiment Station Bulletin No. 1555* (Texas A & M University, College Station, Texas, 1988).

"Engineering Aspects of Insect Cell Suspension Culture: A Review," Wu, J., King, G., Daugulis, A.J., Faulkner, P., Bone, D. H., and Goosen, M. F. A., *Appl. Microbiol. Biotechnol.*, 32, 249–255 (1989).

"Shear Sensitivity of Insect Cells in Suspension", Tramper, J., Williams, J. B., and Joustra, D., *Enzyme Microb. Techno.*, 8, 33–36 (1986).

"Large–Scale Insect Cell–Culture for Recombinant Protein Production," Maiorella, B., Inlow, D., Shauger, A., and Harano, D., *Bio/Technology*, 6, 1406–1410 (1988).

"Sparged Animal Cell Bioreactors: Mechanism of Cell Damage and Pluronic F–68 Protection," Murhammer, D. W. and Goochee, C. F., *Biotechnol. Prog.*, 6, 391–397 (1990).

"Serum–Free Growth and Recombinant EPO Expression in *Spodoptera frugiperda* (Sf–9) Insect Cells," Godwin, G., Belisle, B., De Giovanni, A., Kohler, J., Gong, T., and Wojchowski, D., In Vitro, 25, 19a (1989), abstract No. 36.

"Baculovirus Expression Vectors," Bishop, D. H. L. and Possee, R. D., *Adv. Gene Technol.*, 1, 55–72, (1990).

"Expression of Proteins using Recombinant Baculoviruses," Webb, N.R. and Summers, M. D., *Technique*, 2, 173–188 (1990).

"A Simplified Method for the Production of Recombinant Baculovirus," Goswami, B. B. and Glazer, R. O. *BioTechniques*, 10, 626–630 (1991).

"Production of Human Beta Interferon In Insect Cells Infected with a Baculovirus Expression Vector," Smith, G. E., Summers, M. D., and Fraser, M.J., *Mol. Cell. Biol.*, 3, 2156–2165 (1983).

"Modification and Secretion of Human Interleukin 2 Produced in Insect Cells by a Baculovirus Expression Vector," Smith, G.E., Ju, G., Ericson, B. L., Moschera, J., Lahm, H., Chizzonite, R., and Summers, M. D., *Proc. Nat. Acad. Sci. USA*, 82, 8404–8408 (1985).

"Novel Expression of Chimeric Plasminogen Activators in Insect Cells," Devlin, J. J., Devlin, P. E., Clark, R., O'Rourke, E. C., Levenson, C., and Mark, D. F., *Bio/Technology*, 7, 286–292 (1989).

"Expression of Human Granulocyte–Macrophage Colony–stimulated Factor Gene in Insect Cells by a Baculovirus Vector," Chiou, C. J., and Wu, M. C., *FEB*, 259, 249–253 (1990).

"Bioinsecticides: II. Baculoviridae," Miltenburger, H. G. and Kreig, A., *Advances in Biotechnological Processes*, 3, 291–313 (1984).

"Human Feeding Tests Using a Nuclear–Polyhedrosis Virus of *Heliothis zea*," Heimpel, A. M. and Buchanan, L. K., *J. Invertebr. Pathol*, 9, 55–57 (1967).

Falcon, L. A., "Viral Pesticides: Present Knowledge and Potential Effects on Public and Environmental Health," Summers, M. D. and Kawanishi, C. Y., eds. (Health Effects Research Laboratory, Office of Health and Ecological Effects, U.S. Environmental Protection Agency, Research Triangle Park, NC, 1978), pp. 11–23.

"Protein Production (β–Galactosidase) from a Baculovirus Vector in *Spodoptera frugiperda* and *Trichpolusia ni* Cells in Suspension Culture," Ogonah, O., Shuler, M. L., and Granados, R. R., *Biotechnol. Lett.*, 13, 265–270 (1991).

RECOMBINANT PROTEIN PRODUCTION AND INSECT CELL CULTURE AND PROCESS

ORIGIN OF THE INVENTION

The jointly made invention described herein was made by employees of the United States Government and may be manufactured and used by or for the Government of the United States of America for governmental purposes without the payment of any royalties thereon or therefor.

The invention described herein was also made by inventors in the performance of work under a NASA contract with Krug Life Sciences and a memorandum of understanding with Tulane University and is subject to the provisions of Section 305 of the National Aeronautics and Space Act of 1958, Public Law 85-568 (72 Stat. 435; 42 U.S.C. 2457).

RELATED APPLICATION

This application is a continuation-in-part of U.S. application Ser. No. 08/062,856 entitled Recombinant Protein Production and Insect Cell Culture and Process filed May 14, 1993, now abandoned.

BACKGROUND OF THE INVENTION

In vitro cultures of animal cells are hosts for an increasing assortment of recombinant protein products. This is a relatively new phenomenon, beginning in the mid 1980's. In this short period of time, these proteins have made a substantial contribution to the U.S. economic market. In the pharmaceutical industry alone, biotherapies, which are primarily recombinant proteins, generated $1.2 billion in U.S. sales in 1991 and may grow to nearly $8.0 billion in 2001 as more proteins become commercially available [Thayer, A. M., C & EN, Feb. 25, 27 (1991)]. The market size and its capacity for growth demonstrate the importance of recombinant protein production to the fields of biotechnology and bioengineering.

Recombinant proteins derived from animal cells are employed in a range of disciplines from agriculture to medicine to basic research. During the past decade in medicine, progress has been made in genetic engineering and animal-cell cultivation to produce an increasing assortment of recombinant proteins in sufficient quantities for the development of new drug therapies. The proteins themselves can serve as therapies, or they can be used to identify and test chemotherapies that regulate protein function in vivo. Recombinant tissue plasminogen activator is an example of a protein therapy. It is given to patients with evolving myocardial infarction to dissolve coronary thrombus and restore blood flow to the ischemic area [Longridge, D. J., Foilenfant, M. J., Maxwell, M. P., Ford, A. J., and Hughes B., Cardiovasc. Res., 24, 697 (1990)]. In clinical trials, another protein therapy, erythropoietin, has been used to treat anemia in patients with progressive renal failure [Eschbach, J. W., Kelly, M. R., Haley, N. R., Abels, R. I., and Adamson, J. W., N. Engl. J. Med., 321, 158 (1989)] and sickle cell disease [Goldberg, M. A., Brugnara, C., Dover, G. J., Schapira, L., Charache, S., and Bunn, H. F., N. Engl. J. Med., 323, 366 (1990)]. Examples of protein-regulating chemotherapies include enalapril, an inhibitor of angiotensin-converting enzyme, for the treatment of sickle cell disease. [Falk, R. J., Scheinman, J., Phillips, G., Orringer, E., Johnson, A., and Jennette, J. C., N. Engl. J. Med., 326, 910–915 (1992)]. A chemotherapy derived from azole regulated cytochrome P-450 dependent testosterone biosynthesis [Bossche, H. V., Lauwers W., Willemsens, G., Cools, W., Prog. Clin. Bioi. Res., 185A, 187 (1985)].

At present, both procaryotes and eucaryotes are utilized as hosts for commercial production of recombinant proteins. The choice of one over the other is based on the structural complexity of the protein being produced and the desired yield. If a protein can be produced in a biologically active form from either host, procaryotes are preferred: they grow faster and express more protein than animal cells [Marino, M. H., BioPharm, July/August, 18 (1989); Bebbington, C. and Hentschel, C., Trends Biotechnol., 3, 314 (1985)]. Doubling times are in hours rather than days. Similarly, yields are in grams of protein per liter media rather than milligrams per liter. Eucaryotes are chosen as hosts when procaryotes are unable to produce functional protein [Marino, M. H., BioPharm, July/August, 18 (1989); Bebbington, C. and Hentschel, C., Trends Biotechnol., 3, 314 (1985)]. This typically occurs when the protein requires post-translational modification (e.g., glycosylation, phosphorylation or macromolecular assembly) to be functional. Bacteria cannot perform post-translational modifications at all; simple eucaryotes such as yeast do so to a limited extent; but complex eucaryotes such as animal cells, with few exceptions, perform the entire complement of post-translational modifications.

Commercial production of recombinant proteins from animal cells requires that the production process be reliable, yielding consistent amounts of product with reproducible biological activity. Such stringency has been achieved in vitro from animal cells cultured in a bioreactor which provides a controlled environment for cell growth.

Several bioreactor designs have been employed in the past for the cultivation of animal cells [Merten, 0. W., Trends Biotechnoi., 5, 230 (1987); Nelson, K. L., BioPharm., February, 42 (1988); Tramper, J., Smit, D., Straatman, J., and Vlak, J. M., Bioprocess Eng., 3, 37 (1988)]. These include a stirred-tank reactor, a hollow-fiber reactor containing porous fiber bundles in which cells grow, and an airlift reactor in which gas bubbles rise through a draft tube lifting the culture fluid to the top of the reactor where it returns to the bottom through the annular space between the draft tube and outer shell of the reactor. [See Inlow et al., U.S. Pat. No. 5,024,947, entitled "SerumFree Media For the Growth on Insect Cells and Expression of Products Thereby", issued Jun. 18, 1991]. Bioreactors up to 10,000 liters in size are used in industry for animal cells [Rhodes, M., Genetic Engineering News, 10, March, 7 (1990)]. Choosing the size and type of bioreactor for a particular process depends on a number of factors such as market demand, cell properties and yield. Hollow-fiber reactors are currently limited to volumes on the order of one liter [Cracauer et al., U.S. Pat. No. , 4,804,628, entitled "Hollow Fiber Cell Culture Device and Method of Operation" issued Feb. 14, 1989; Nelson, K. L., BioPharm., March, 34 (1988)]. Airlift reactors can not readily keep microcarrier cultures (attachment-dependent cells growing bound to beads that are typically 100 μm in diameter) well mixed [Merten, O. W., Trends Biotechnol., 5,230 (1987)]. The stirred-tank reactor is the system of choice for many companies because of its flexibility: it can support the growth of both suspension and anchorage-dependent cells, can be operated in different feed modes, and can be scaled up to very large volumes (10,000 liters) [Nelson, K. L., BioPharm., March, 34 (1988); Nelson, K. L., BioPharm., February, 42 (1988)].

In bioreactors, mixing is essential for cell proliferation: it supplies cells with nutrients and oxygen, maintains a homogenous environment throughout the reactor, and prevents cells from settling. But in conventional bioreactors, mixing can also cause cell damage from sufficiently large hydrodynamic forces. In a stirred tank, for example, cell damage has been attributed to two mixing phenomena: bulk-fluid turbulence and gas/liquid interfaces [O'Connor, K. C. and Papoutsakis, E. T., *Biotechnol. Tech.*, 6, 323 (1992); Kunas, K. T. and Papoutsakis, E. T., *Biotechnol. Bioeng.*, 36, 476–483 (1990)]. Typically, these interfaces arise during cultivation as a result of sparging, vortex formation, turbulent eddies, fluid-wall shear gradients and surface oxygenation. Cell damage from bulk-liquid turbulence has been correlated to the ratio of the Kolmogorov-scale eddy size to bead diameter for microcarrier cultures [Cherry, R. S. and Papoutsakis, E. T., *Bioprocess Eng.*, 1, 29–41 (1986); Croughan, M. S., Hamel, J. F., and Wang, D. I. C., *Biotechnol. Bioeng.*, 29, 130–141 (1987)] and cell diameter for suspension cultures [Kunas, K. T. and Papoutsakis, E. T., *Biotechnol. Bioeng.*, 36, 476–483 (1990); McQueen, A., Meilhoc, E., and Bailey, J. E., *Biotechnol. Letters*, 9, 831 (1987)]. Damage initiates as the ratio approaches unity and intensifies at lower values. It has been proposed that eddies of the same size or smaller than cell particles (microcarrier beads or individual cells) cause high shear stresses on the cell surface, interparticle collisions and reactor-particle collisions [Cherry, R. S. and Papoutsakis, E. T., *Bioprocess Eng.*, 1, 29–41 (1986)]. For larger eddies, shearing and collisions are minimized as cell particles move in eddy streamlines.

Because animal cells are not enclosed in a cell wall like bacteria, they are susceptible to hydrodynamic forces within a bioreactor. Agitation, shear and other hydrodynamic phenomena have a profound effect on cell morphology and physiology which can result in cell damage and death. From a morphological perspective, hydrodynamic forces alter cell shape, adhesion, membrane integrity and spreading [O'Rear, E. A., Udden, M. M., McIntire, L. V., and Lynch E. C., *Biochim. Biophys. Acta*, 691, 274 (1982); Lawrence, M. B., McIntire, L. V., and Eskin, S. G., *Blood*, 70, 1284 (1987); Ives, C. L., Eskin, S. G., and McIntire, L. V., *In Vitro Cell. Dev. Biol.* 22, 500 (1986)]. These morphological changes are accompanied by and related to physiological changes in DNA synthesis, mRNA synthesis and cytoskeletal rearrangement to name a few [O'Connor, K. C. and Papoutsakis, E. T., *Biotechnoi. Tech.*, 6, 323 (1992); Diamond, S. L., Sharefkin, J. B., Dieffenbach, C., Frasier-Scott, D., McIntire, L. V., and Eskin, S. G., *J. Cell. Physiol*, 143, 364–371 (1990); Sato, M., Levesque, M. J., and Nerem, R. M., *Arteriosclerosis*, 7, 276 (1987)]. There are several mechanisms by which these hydrodynamic effects can cause cell death, including lysis from loss of membrane integrity, detachment of anchorage-dependent cells from surfaces, and reduced metabolic activity [O'Connor, K. C. and Papoutsakis, E. T., *Biotechnol. Tech.*, 6, 323 (1992); Croughan, M. S., Hamel, J. F., and Wang, D. I. C., *Biotechnol. Bioeng.*, 33, 731–744 (1989); Petersen, J. F., McIntire, L. V., and Papoutsakis, E. T., *J. Biotechnol.*, 7, 229 (1988)].

Insect cells are distinctly different from animal cells. Very little is known about insect cell metabolism. There is a relatively small body of literature on the subject. Insects and vertebrate animals are classified in totally different phylogenetic systems. Consequently, insect cells have undergone a metabolic evolution that was completely independent compared to animal cell metabolic evolution. Insects have a unique life cycle and, as such, have distinct cellular properties. One of these is the lack of intracellular plasminogen activators in insect cells which are present in vertebrate cells. These differences were highlighted when investigators began to express recombinant intact human plasminogen in Sf9 cells after unsuccessful attempts in vertebrate cells. [Whitefleet-Smith, J., Rosen, E., McLinden, J., Ploplis, V. A., Fraser, M. J., Tomlinson, J. E., McLean, J. W., and Castellino, F. J., *Arch. Biochem. Biophys.*, 271, 390 (1989)]. In the latter, plasminogen is rapidly converted by the activators to plasmin. Other differences include high expression levels of protein products ranging from 1 to greater than 500 mg/liter [Marino, M. H., BioPharm, July/August, 18 (1989)] and ease at which DNA can be cloned into the cells [Fraser, M. J., *In Vitro Cell. Dev. Biol.*, 25, 225 (1989); Summers, M.D. and Smith, G. E., *A Manual of Methods for Baculovirus Vectors and Insect Cell Culture Procedures*, Texas Agricultural Experiment Station Bulletin No. 1555 (Texas A & M University, College Station, Tex., 1988)], both of which make insect cells exceptional hosts for protein production.

Cultivation of insect cells is difficult particularly on a large scale or at a high cell density since they are more sensitive to hydrodynamic forces in a bioreactor [Wu, J., King, G., Daugulis, A. J., Faulkner, P., Bone, D. H., and Goosen, M. F. A., *Appl. Microbiol. Biotechnol.*, 32, 249 (1989); Tramper, J., Williams, J. B., and Joustra, D., *Enzyme Microb. Techno.*, 8, 33 (1986)] and have a greater oxygen uptake rate than most vertebrate cells [Maiorella, B., Inlow, D., Shauger, A., and Harano, D., Bio/Technology, 6, 1406 (1988)]. The oxygen uptake rate has been calculated to be $4\times10^{-10}$ mole cell$^{-1}$ hr$^{-1}$ for Trichoplusia ni cells [Maiorella, B., Inlow, D., Shauger, A., and Harano, D., Bio/Technology, 6, 1406 (1988)] as compared to 0.1 to $2\times10^{-10}$ mole cell$^{-1}$ hr for typical vertebrate cells [Nelson, K. L., BioPharm., March, 34 (1988)]. Upon infection with baculovirus, the oxygen uptake rate for insect cells further increases by upwards of 30% [Kamen, A. A., Tom, R. L., Caron, A. W., Chavarie, C., Massie, B., and Archambault, J., *Biotechnol. Bioeng.*, 38, 619 (1991)]. The sensitivity to hydrodynamic forces is so severe that growth of a Lepidopteran cell line, the fall armyworm ovary *Spodoptera frugiperda* (Sf9), is completely inhibited in bench-scale sparged stirred tanks or airlift bioreactors unless surfactant is added to protect the cell membrane [Murhammer, D. W. and Goochee, C. F., Biotechnol. Prog., 6, 391 (1990)].

The combination of enhanced respiration and hydrodynamic sensitivity places severe constraints on cell oxygenation: sufficient oxygen must be transported to the insect cells for respiration without inducing hydrodynamic damage to the cells. When the oxygen requirements of insect cells are not met, the culture is adversely affected. Under these conditions, the culture is hypoxic or anoxic. We have conducted extensive investigations of anoxic cultures of Sf9 cells [Hugler, W., "Protein Expression of Sf9 Cells Under Stress and Simulated Microgravity," Thesis, Tulane University (1994)]. Within the first three hours of anoxia, cell growth is arrested, total protein synthesis is reducedby 20%, and stress proteins are induced. If anoxia is continued for longer periods of time, cell death is evident. Others have observed that hypoxia reduces the yield of recombinant protein derived from insect cells by a factor of 5 [Scott, R.I., Blanchard, J. H., and Ferguson, C. H. R., Enzyme Microb. Technol., 14, 798 (1992)].

Several different types of bioreactors have been used for insect-cell cultivation. Most of them adequately address cell oxygenation but at the expense of the cell's hydrodynamic sensitivity. Stirred tanks typically oxygenate cells by sparging and impeller stirring of growth medium, generating hydrodynamic forces from both the mixing and bursting air bubbles at gas/liquid interfaces. Spin-filter adapters for stirred tanks provide bubble-free oxygenation, although substantial impeller stirring is still required [Avegerinos, G. C., Drapeau, D., Socolow, J. S., Mao, J.-I., Hsiao, K., and Broeze, R. J., *Biotechnology*, 8, 54 (1990)]. Airlift bioreactors are designed to eliminate hydrodynamic damage to the cells from impellers as mixing is achieved by rising gas bubbles [Inlow et al., U.S. Pat. No. 5,024,947, entitled "Serum Free Media For the Growth on Insect Cells and Expression of Products Thereby", issued June 18, 1991]. This design is flawed, however, in that by eliminating one source of hydrodynamic damage it increases another—air/liquid interfaces. The detrimental effect of impeller mixing and air/liquid interfaces on insect-cell culture has been documented [Murhammer, D. W. and Goochee, C. F., *Biotechnol. Prog.*, 6, 391 (1990); Chalmers, J. J. and Bavarian, F. *Biotechnol. Prog.*, 7, 151 (1991)].

Two reactor designs that consider the hydrodynamic sensitivity of insect cells are roller bottles and microencapsulation. In roller bottles, cells are mixed by the end-over-end rotation of the reactor instead of by an impeller [Inlow et al., U.S. Pat. No. 5,024,947, entitled "Serum Free Media For the Growth on Insect Cells and Expression of Products Thereby", issued Jun. 18, 1991]. In this environment, cells grow attached to the reactor wall rather than in suspension. As such, cell densities that are achieved in roller bottles are far less than in suspension cultures because growth is limited by the surface area of the reactor wall. In addition, roller bottles are not conducive to scale up to the large volumes required for commercial cultivation. Another approach to insect-cell cultivation is to encapsulate the cells within porous microbeads [King, G. A., Daugulis, A. J., Faulkner, P., Bayly, D., and Goosen, M. F. A., *Biotechnol. Lett.*, 10, 683 (1988)]. This shields the cells from the hydrodynamic forces on the outside of the beads. The difficulty with this design is the possibility of cell aggregation and accumulation of waste products within the beads at high cell density. The wastes (e.g. ammonia and lactate) are byproducts of cell metabolism and adversely affect cell health at high concentrations [Petersen, J. F., McIntire, L. V., and Papoutsakis, E. T., *Biotechnol.*, 7, 229 (1988)]. Cell aggregation is an important issue for both mammalian and insect cells where hydrodynamic forces are minimized. These cell types will frequently adhere to surfaces through proteins on the cell surface [Ben-Ze'ev, A., Farmer, S. R., and Penman, S. *Cell.*, 21, 365 (1980)]. In slow turning vessels, cells can aggregate into structures several millimeters in diameter [Becker, J. L., Prewett, T. L., Spaulding, G. F., and Goodwin, T. J., *J. Cell Biochem.*, 51, 382 (1993)]. The cores of such aggregates often become hypoxic or anoxic [Coleman, C. N. *Semin. Oncol.*, 16, 169 (1989)]. For insect cells, oxygen deprivation of this type would lower recombinant proteins yields as described above.

Developing a bioreactor environment which achieves favorable conditions for insect-cell growth through a reduction in hydrodynamic forces is a topic of much interest today and is the focal point of this invention. The invention described here is a specific non-animal cell culture process that incorporates both reduced hydrodynamic forces and enhanced cell oxygenation. The culture is maintained as a single-cell suspension, instead of in an aggregated state. Waste byproducts are kept at lower concentrations than in conventional bioreactors. Combined these features create an environment that improves cultivation and fundamentally changes cell metabolism.

Much of the cultivation and production research on insect cells has been performed with Sf9 cells [Wu, J., King, G., Daugulis, A. J., Faulkner, P., Bone, D. H., and Goosen, M. F. A., *Appl. Microbiol. Biotechnol.*, 32, 249 (1989); Maiorella, B., Inlow, D., Shauger, A., and Harano, D., *Bio/Technology*, 6, 1406 (1988); Godwin, G., Belisle, B., De Giovanni, A., Kohler, J., Gong, T., and Wojchowski, D., In Vitro, 25, 17a (1989)]. This cell line is frequently chosen because it grows more robustly than other insect cells, is an immortal cell line, can be adapted from attachment-dependent to attachment-independent growth, is an exceptional host for recombinant protein production as described in the following paragraph, can grow in serum-free media and is commercially available [Fraser, M. J., *In Vitro Cell. Dev. Biol.*, 25, 225 (1989); Wu, J., King, G., Daugulis, A. J., Faulkner, P., Bone, D. H., and Goosen, M. F. A., Appl. *Microbiol. Biotechnol.*, 32, 249 (1989); Godwin, G., Belisle, B., De Giovanni, A., Kohler, J., Gong, T., and Wojchowski, D., In Vitro, 25, 17a (1989)]. Individual Sf9 cells have diameters from 10 to 20 μm and can be maintained by following standard published protocols known to those skilled in the art of animal cell culture with the following exceptions that are distinctly different from typical animal culture protocols: they grow optimally at 27 rather than 37° C., external $CO_2$ is not required for growth, and the optimal pH for growth media is 6.2 instead of 7.4 [Fraser, M. J., *In Vitro Cell. Dev. Biol.*, 25, 225 (1989); Godwin, G., Belisle, B., De Giovanni, A., Kohler, J., Gong, T., and Wojchowski, D., *In Vitro*, 25, 17a (1989)].

Sf9 shows great promise as an animal-cell host for the production of recombinant proteins. One of the reasons is the ease at which proteins can be cloned, expressed and purified relative to vertebrate animal cells. Sf9 more readily accepts foreign genes coding for recombinant proteins than many vertebrate animal cells because it is very receptive to viral infection and replication [Bishop, D. H. L. and Possee, R. D., *Adv. Gene Technol.*, 1, 55, (1990)]. Expression levels of recombinant proteins are extremely high in Sf9 and can approach 500 mg/liter [Webb, N. R. and Summers, M. D., Technique, 2, 173 (1990)]. The cell line performs a number of key post-translational modifications; however, they are not identical to those in vertebrates and, therefore, may alter protein function [Fraser, M. J., *In Vitro Cell. Dev. Biol.*, 25, 225 (1989)]. Despite this, the majority of recombinant proteins that undergo post-translational modification in insect cells are immunologically and functionally similar to their native counterparts [Fraser, M. J., *In Vitro Cell. Dev. Biol.*, 25, 225 (1989)]. In contrast to animal cell culture, Sf9 facilitates protein purification by expressing relatively low levels of proteases and having a high ratio of recombinant to native protein expression [Goswami, B. B. and Glazer, R. O. BioTechniques, 10, 626 (1991)].

There has been an explosive growth in the number of proteins that have been expressed in Sf9 with less than 10 by 1985 to over 100 by 1990. These include β-interferon [Smith, G. E., Summers, M. D., and Fraser, M. J., *Mol. Cell. Biol.*, 3, 2156 (1983)], interleukin-2 [Smith, G. E., Ju, G., Ericson, B. L., Moschera, J., Lahm, H., Chizzonite, R., and Summers, M. D., *Proc. Nat. Acad. Sci. USA*, 82, 8404 (1985)], chimeric plasminogen activators [Devlin, J. J., Devlin, P. E., Clark, R., O'Rourke, E. C., Levenson, C., and Mark, D. F., *Bio/Technology*, 7, 286 (1989)]and macrophage colony stimulating factor [Chiou, C. J., and Wu, M. C., FEB, 259, 249 (1990)]to name a few.

Baculoviruses serve as expression systems for the production of recombinant proteins in insect cells. These viruses are pathogenic towards specific species of insects, causing cell lysis [Webb, N. R. and Summers, M. D., *Technique*, 2, 173 (1990)]. They are, and have been, a natural part of the ecosystem where they control the population size of their hosts [Miltenburger, H. G. and Kreig, A.,

*Advances in Biotechnological Processes*, 3, 291 (1984)]. Some 300 species of baculovirus have been isolated. They are nonhazardous to humans, other vertebrates and indeed most invertebrates. After acute exposure of baculovirus from *Autographa californica, Mamestra brassicae* and *Cydia pomonella*, NMRI mice and Chinese hamsters had no chromosomal aberrations or health disturbances [Miltenburger, H. G. and Kreig, A., *Advances in Biotechnological Processes*, 3, 291 (1984)]. Similarly, physical examinations and laboratory tests failed to detect any abnormalities in humans given various baculoviruses orally [Heimpel, A. M. and Buchanan, L. K., *J. Invertebr. Pathol,* 9, 55 (1967)].

Baculoviruses are desirable alternatives to conventional chemical insecticides for agricultural pest control because of their selective pathogenicity towards targeted insects, nonpathogenicity towards vertebrates and compatibility with the ecosystem. At least three baculoviruses have been registered by the Environmental Protection Agency for commercial distribution as insecticides: the baculoviruses of *Heliothis zea, Orgyia pseudotsugata* and *Lymantria dispar* [Miltenburger, H. G. and. Kreig, A., *Advances in Biotechnological Processes,* 3, 291 (1984)]. Baculovirus has been successfully tested to control insect populations in Sweden, the Soviet Union, Italy, Canada and the United States [Miltenburger, H. G. and Kreig, A., *Advances in Biotechnological Processes,* 3, 291 (1984)]. At present, chemical insecticides are the primary means of controlling pest populations. Their use, however, is facing growing opposition-they pollute the environment, and insects may become resistant to their effects. It is estimated that 30% of the agricultural pests in the Western Hemisphere can be controlled by insect viruses [Falcon, L. A., in *Viral Pesticides: Present Knowledge and Potential Effects on Public and Environmental Health,* Summers, M. D. and Kawanishi, C. Y., eds. (Health Effects Research Laboratory, Office of Health and Ecological Effects, U.S. Environmental Protection Agency, Research Triangle Park, NC, 1978), p.11]. This is a significant figure. Substituting baculovirus for its chemical counterpart in these cases could substantially reduce the total amount of chemical insecticides used in the environment.

Recombinant protein expression in insect cells is achieved by viral infection or stable transformation. For the former, the desired gene is cloned into baculovirus at the site of the wild-type polyhedron gene [Webb, N. R. and Summers, M. D., *Technique,* 2, 173 (1990); Bishop, D. H. L. and Possee, R. D., *Adv. Gene Technol.,* 1, 55, (1990)]. The polyhedron gene is nonessential for infection or replication of baculovirus. It is the principle component of a protein coat in occlusions which encapsulate virus particles. When a deletion or insertion is made in the polyhedron gene, occlusions fail to form. Occlusion negative viruses produce distinct morphological differences from the wild-type virus. These differences enable a researcher to identify and purify a recombinant virus. In baculovirus, the cloned gene is under the control of the polyhedron promoter, a strong promoter which is responsible for the high expression levels of recombinant protein that characterize this system. Expression of recombinant protein typically begins within 24 hours after viral infection and terminates after 72 hours when the Sf9 culture has lysed.

Stably-transformed insect cells provide an alternate expression system for recombinant protein production [Jarvis, D. L., Fleming, J.-A. G. W., Kovacs, G. R., Summers, M. D., and Guarino, L. A., *Biotechnology,,* 8, 950 (1990); Cavegn, C., Young, J., Bertrand, M., and Bernard, A. R., in *Animal Cell Technology: Products of Today, Prospects for Tomorrow,* Spier, R. E., Griffiths, J. B., and Berthold, W., Eds. (Butterworth-Heinemann, Oxford, 1994, pp. 43–49)]. In these cells, the desired gene is expressed continuously in the absence of viral infection. Stable transformation is favored over viral infection when recombinant protein production requires cellular processes that are compromised by the baculovirus. This occurs, for example, in the secretion of recombinant human tissue plasminogen activator from Sf9 cells [Jarvis, D. L., Fleming, J.-A. G. W., Kovacs, G. R., Summers, M. D., and Guarino, L. A., *Biotechnology,,* 8, 950 (1990)]. Viral infection is favored when the recombinant protein is cytotoxic since protein expression is transient in this system.

SUMMARY OF THE INVENTION

Insect cells have shown unusual promise for recombinant protein product. This is dependent upon a large scale production system that provides the proper environment. The subject of this invention is recombinant protein production using a unique process for insect cell culture. Higher expression rates and greater yields that can be realized with the new production systems will increase the variety of protein products and lower their cost to consumers. This can result in, for example, new biotherapies to treat disease, more sensitive diagnostic agents that will detect life-threatening illness sooner, and natural insecticides that have greater species specificity. Because recombinant proteins are germane to many disciplines, this invention will have a fundamental impact in many areas of investigation. This invention can be used for commercial protein production.

A new process system has been discovered for in vitro cultivation of shear-sensitive, invertebrate cells, specifically insect cells, and for the production of recombinant proteins from these cells. Insect cells were cultivated in a bioreactor which is a horizontally rotating culture vessel designed to create low shear by modulating the rotation, preferably in a bioreactor called the High Aspect Ratio Vessel (HARV) described in the published patent application by the National Aeronautics and Space Administration in the Scientific and Technical Aerospace Reports Volume 29/Number 9, May 8, 1991, ACC NOS. N91-17531, U.S. Ser. No. 625,345 now U.S. Pat. No. 5,153,131, entitled "A Culture Vessel With Large Perfusion Area to Volume Ratio," invented by David A. Wolf, Clarence F. Sams and Ray P. Schwarz and filed on December 11, 1990 and issued Oct. 6, 1992, which patent is incorporated by reference in its entirety in this specification.

The present invention achieves cell culture without cell aggregation in the HARV or any other low-turbulence environment. Prior experience with HARV cultivation is characterized by animal, especially mammalian cell aggregation into three-dimensional spheroids up to several millimeters in diameter. However, aggregation on this scale would cause hypoxia in insect cells having high oxygen uptake rates and, thus, reduce product yield. For this invention, inoculation and culturing conditions were selected to minimize or essentially eliminate aggregation. As such, aggregation was negligible; insect cells grew in the HARV as a suspension of single cells or as aggregates of only a few cells. Under these culturing conditions, there was no indication of hypoxia or anoxia. This is contrary to prior applications of the HARV to promote cell aggregation particularly in mammalian systems.

The insect cells were used for production of recombinant polypeptides herein defined as any type of polypeptide, protein or virus. For the purposes of this invention the terms polypeptide and protein are not intended to limit the scope of production of any selected amino acid sequence. The insect cells are selected and transformed to include a selected DNA sequence encoding the desired polypeptide product.

Under the terms of the Budapest Treaty on the International Recognition of the Deposit of Microorganisms for the Purpose of Patent Procedure, "RES" insect cells were deposited with the American Type Culture Collection (ATCC) of Rockville, Md., USA, on Dec. 12, 1996, and was given ATCC designation number ATCC CRL-12244.

Applicant's co-assignees, NASA and Tulane University represent that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 C.F.R. 1.14 and 35 U.S.C. §122. The deposited material will be maintained with all the care necessary to keep it viable and uncontaminated for a period of at least thirty (30) years after the date of deposit or for the enforceable life of the patent, whichever period is longer. Applicant's co-assignees acknowledge its duty to replace the deposit should the depository be unable to furnish a sample when requested due to the condition of the deposit. The cells are then cultured in the HARV which is a horizontally rotating culture vessel designed to create low shear conditions by modulating the rotation. The insect cells cultured by this process recombinantly produce the selected polypeptide which can then be collected and purified. The DNA sequence encoding the desired polypeptide is introduced into insect cells byviral infection or stable transformation. For the latter, the DNA sequence is incorporated into the cell's own DNA and is expressed continuously throughout the life cycle of the cell. The former utilizes an insect pathogenic virus, specifically a baculovirus, cloned with the selected DNA sequence. This sequence is expressed transiently in insect cells, as the virus eventually kills the cells. If desired, selected DNA sequences can be used in the transformation process that promote the expression of the DNA sequence encoding the polypeptide. Selective initiation methods for producing the recombinant polypeptide may also be utilized. For instance, a regulation sequence that can turn on protein production by exposure to certain conditions or in the presence of certain compounds can be included in the DNA sequence used to transform the insect cells. In an alternative process, the insect cells are used as hosts for virus production. The virus may be wild type or transformed. Lepidoptera cells are a preferred cell for transformation, and other insect cells that can be cultured by the process of this invention may be used. The insect cells may be cultured in a HARV or other vessel prior to transformation.

The insect cells cultured by the process of this invention produce a cell line with unique and unexpected characteristic metabolism regardless of the genetic transformation to produce a new cell line. The metabolically transformed Lepidoptera cell line of this invention has been designated RES. Specifically, both non-infected and baculovirus-infected RES utilize an alternate metabolic pathway as compared to their Sf9 counterparts characterized by pH change, glucose and amino acid consumption, and lactic acid production. Accordingly, transformations can be viral or metabolic or both.

An alternative process of this invention utilizes an insect pathogenic virus to produce recombinantly the selected polypeptide using the insect cells as a host. The preferred virus is a baculovirus. The virus is prepared to include the incorporation of the selected DNA sequence encoding the polypeptide. Other DNA sequences to promote or enhance the expression and production of the polypeptide may also be included in the incorporated DNA sequence. The insect cells are cultured as described herein and the selected virus is transferred into the culture vessel inoculating the insect cells. The virus infects the insect cells and uses the insect cells as a host to replicate and produce the encoded polypeptide. The polypeptide may be collected and purified as desired.

In the preferred process using the HARV, insect cells were grown in a liquid medium suspension without support matrices such as microcarrier beads. Aggregation was negligible. In the HARV, the growth and metabolic profile for these insect cells were profoundly different than those obtained using conventional cultivation techniques. Specifically, stationary phase in the HARV was extended from 24 hours to at least 7 days while cell concentration and viability remained in excess of $1\times10^7$ viable cells/ml and 90%, respectively. Measurements of glucose utilization, lactate production, ammonia production and pH change indicate that HARV cultivation had a two-fold effect on cell metabolism. Less nutrients were consumed and less wastes were produced in stationary phase by as much as a factor of 4 over that achieved with conventional vessels. Those nutrients that were consumed in the HARV were directed along different metabolic pathways as evidenced byan extreme shift in glucose utilization from consumption to production in lag phase and a decrease in yield coefficients by one half in stationary phase. These results suggest that cultivation of insect cells in the HARV may reduce production costs of cell-derived biologicals by extending production time and reducing medium requirements.

Further distinctions between the process of this invention and conventional cultivation were observed after insect cells were infected with recombinant baculovirus coding for the protein β-galactosidase (β-gal). Using the process of the present invention, the cultures infected at a concentration of $1.3\times10^5$ viable cells/ml with a multiplicity of infection (MOI) of 10 continued to grow for a period of 35 hours after infection to $1.7\times10^6$ while retaining a viability that exceeded 90%. Under the same infection conditions, conventional cultivation in shaker flasks resulted in a loss in viable cell concentration within 24 hours after infection. In fact, viable cell concentration remained higher in the HARV throughout the 180 hours of cultivation by approximately a factor of 2 or greater. These higher concentrations can result in a greater yield of baculovirus and recombinant protein from the HARV culture. Moreover, these results are illustrative of alternate metabolic pathway usage. Not only does this represent a new process for expressing protein, but enables the production of pathogenic virus for use as an insecticide.

Production of recombinant β-gal using the present invention surpassed that achieved in shaker flasks. For the infection conditions described in the previous paragraph, the amount of β-gal present was greater by a factor of 2 to 7 during cultivation, resulting in a total yield of protein that ranged from 8 to 33 units of β-gal/ml medium. A unit of β-gal is defined as the amount of the enzyme required to hydrolyze 1.0μmole/min o-nitrophenyl-β-D-galactopyranoside (ONPG) at pH 7.3° and 37° C.

BRIEF DESCRIPTION OF THE DRAWINGS

FIG. 1A growth & FIG. 1B viability profiles HARV cultures of RES cells (●) and shaker culture of Sf9 cells (o). Experimental conditions for cultivation are described in the Detailed Description of the Invention and are summarized in Table 1.

Figure 1A:
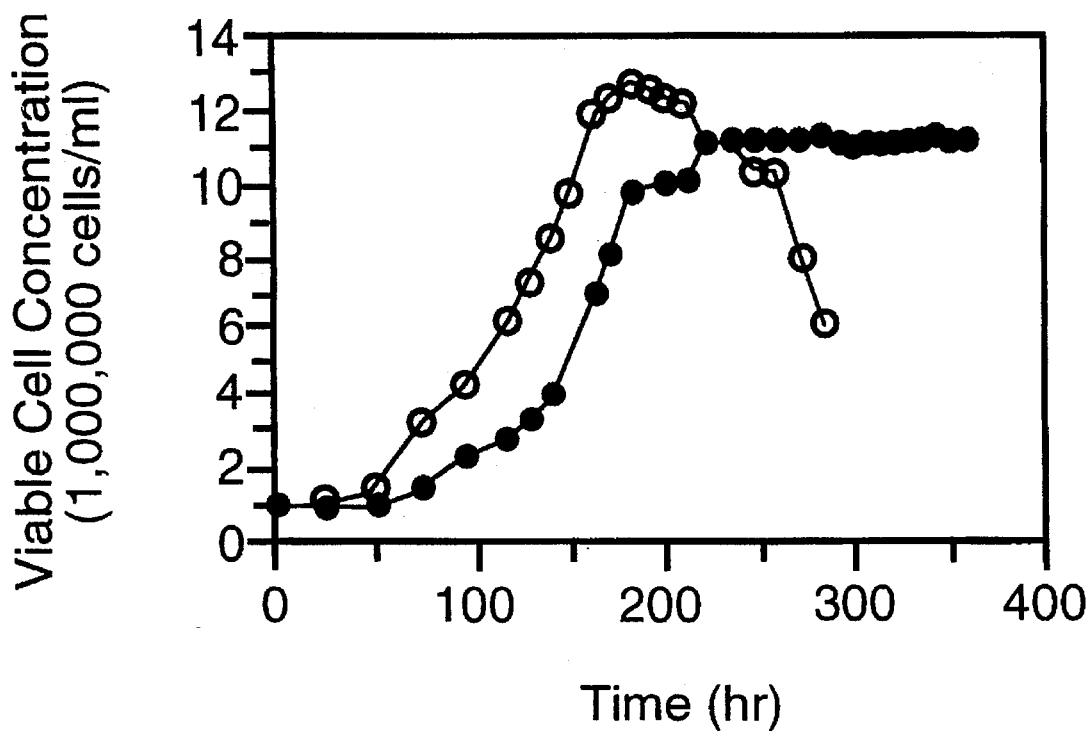
FIGS. 1A and 1B.
Figure 1B:
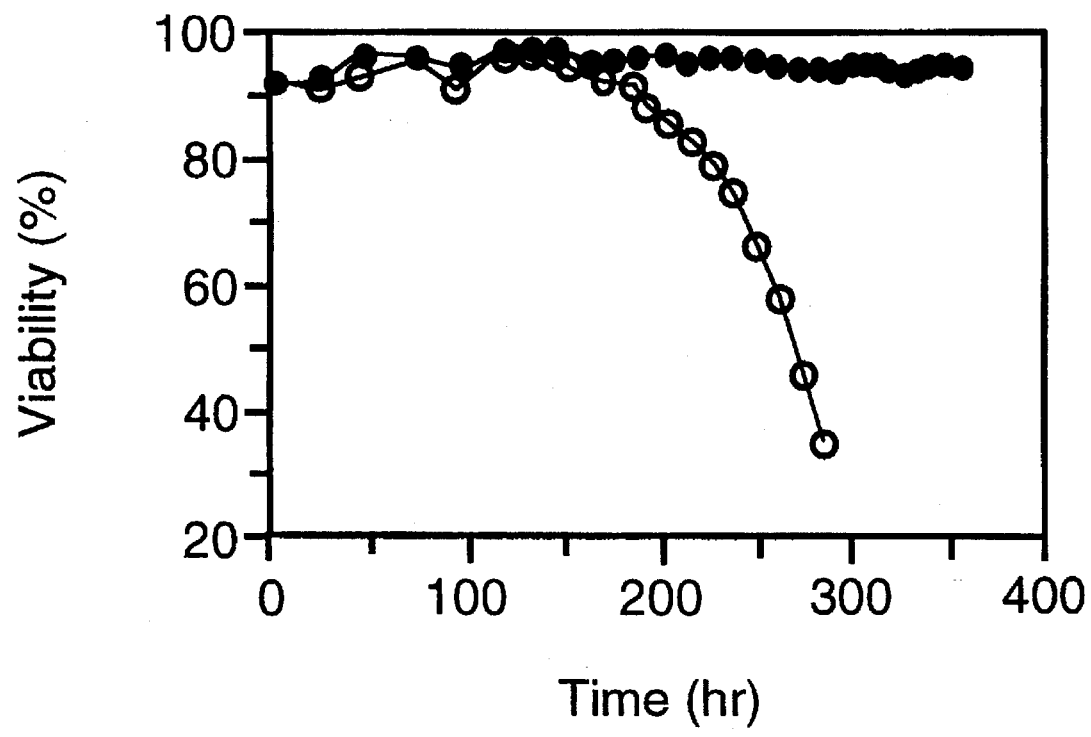
Figure 2:
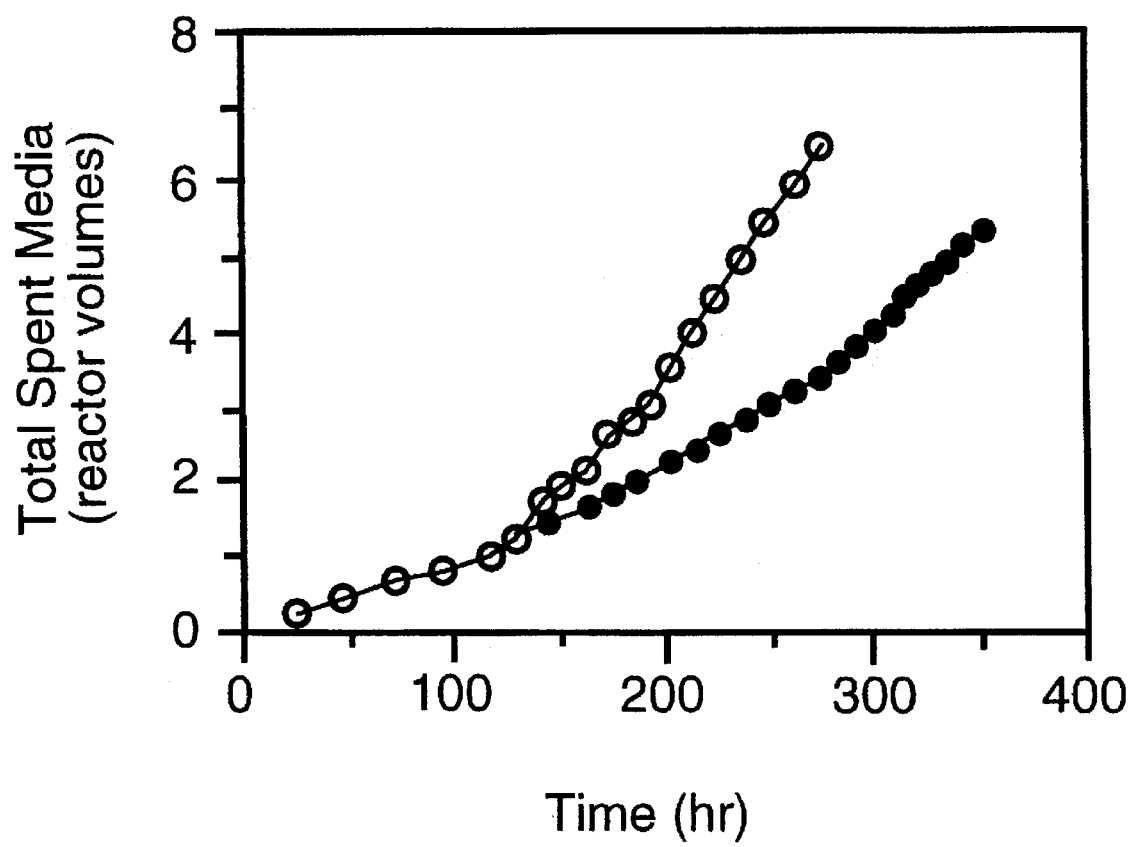
FIG. 2. A comparison of medium replacement in the HARV (•) versus shaker flask (o). Medium replacement is quantified as the accumulation of spent medium removed from each vessel.

For FIGS. 1 through 3, each data point represents the average of four measurements from two separate cultures, two measurements per culture. Measurements had uncertainties of no more than 5% each.

DETAILED DESCRIPTION OF THE INVENTION

Insect cells for in vitro cultivation have been produced and several cell lines are commercially available. This process includes using insect cells capable of culture as described herein regardless of the source. The preferred cell line is Lepidoptera Sf9 cells. Other cell lines include Drosophila cells from the European Collection of Animal Cell Cultures (Salisbury, UK) or cabbage looper *Trichoplusia ni* cells including High Five available from Invitrogen Corp. (San Diego, Calif.) Sf9 insect cells from either Invitrogen Corporation or American Type Culture Collection (Rockville, Md.) are the preferred cell line and were cultivated in the bioreactor freely suspended in serum-free EX-CELL 401 Medium purchased from JRH Biosciences (Lenexa, Kans.) and maintained at 27° C. The preferred bioreactor is the HARV as described above. The metabolically transformed cell line RES derived from the Sf9 cells was cultivated in the HARV using the process of this invention.

Specifically, cells are suspended in growth medium and mixed by the horizontal rotation of the vessel itself rather than by an impeller, greatly reducing turbulent eddy formation and reactor-cell collisions. To further reduce hydrodynamic forces, aeration in the HARV is bubble free, eliminating hydrodynamic damage to the cells at air/liquid interfaces. In addition, medium and chamber wall rotate as a solid body at the same angular velocity, eliminating shear forces at this interface. Combined, this reduction in fluid forces makes the HARV an exceptionally quiescent culturing environment. In fact, the total forces acting on a unit area of cell surface in the HARV are estimated to be less than 0.5 dyne/cm$^2$. The horizontal rotation of the culture vessel is modulated to create the low shear conditions. Typically, low shear conditions favor cell aggregation, but the insect cells have been successfully cultured without aggregation.

A 125 ml shaker flask containing 50 ml medium served as the control vessel in this study because it provides one of the most gentle forms of convention cultivation. The vessel was mixed on a Bellco (Vineland, N.J.) orbital shaker at a rotational speed, 100 rpm, which is optimal for cell growth. While quiescent, a shaker flask generates more hydrodynamic forces than the HARV. When operated at 100 rpm, the maximum shear stress at the flask wall is greater than 1.0 dyne/cm$^2$ [Cherry, R. S. and Papoutsakis, E. T., *Bioprocess Eng.*, 1, 29–41 (1986)]. For comparison, most conventional bioreactors operate near 5.0 dyne/cm$^2$. Because shaker flasks generate relatively low levels of turbulence, differences observed in culture performance between the HARV and shaker flask should be applicable and most likely magnified in comparisons between the HARV and more turbulent bioreactors.

To inoculate the 50 ml HARV, it was first filled with 15 ml of medium to act as a cushion for the suspended Sf9 cells as they were pipetted into the vessel. Twenty-five milliliters of 2×10$^6$ viable cells/ml was added next. An additional 10 ml of medium was used to fill the vessel. Two 5-ml syringes half-filled with medium were attached to the small ports and manipulated to remove all air bubbles from the vessel. One syringe was removed, the open small port was capped, and one syringe remained attached for pressure equalization. The vessel was screwed into its base. The initial rotation speed was set at 11 or 12 rpm, with adjustments made to modulate the rotation to minimize turbulence while maintaining a cellular suspension.

Both pH and glucose were monitored to determine the frequency of cell feeding in the HARV and shaker flask. A Yellow Springs Instrument (YSI) Model 27 Industrial Analyzer (Yellow Spring, Ohio) was used to enzymatically detect glucose (YSI kit 2365). In the two vessels, cells were fed by replacing cell-free spent medium with fresh medium to maintain a glucose level of 100–250 mg/dl and pH between 5.9 and 6.4. For medium replacement in the HARV, vessel rotation was first stopped. The culture remained stationary for about 5 minutes until the medium near the top port had clarified. Conditioned medium (10 ml) was removed through the top port and replaced with fresh medium. Air bubbles were eliminated from the vessel, and rotation was resumed.

Inoculation and culture conditions in the HARV were designed to minimize cell aggregation. Specifically, the vessel was inoculated with a relatively low concentration of Sf9 cells (2×10$^6$ viable cell/ml). This greatly reduced nucleation of cell aggregates as the inoculum passed through a narrow port into the HARV. In addition, cell-cell adherence was inhibited by a surfactant, Pluronic F-68(Sigma Chemical Co., St. Louis, Mo.), in the Ex-Cell 401 medium. The surfactant is present in the medium to coat the outer membrane of fragile insect cells, protecting them from hydrodynamic forces during cultivation [Murhammer, D. W. and Goochee, C. F., *Biotechnol. Prog.*, 6, 391 (1990)]. In doing so, it also limits interaction between surface proteins that cause cell-cell adherence. When Sf9 cells were cultured in the HARV in this manner, aggregation was negligible. The cells grew as a suspension of single cells or aggregates of only a few cells.

When preferred cultivation conditions were not followed, aggregation did occur in the HARV. For example, inocula containing greater than 2×10$^6$ viable cells/ml produced aggregates in non-infected cultures grown in the presence of Pluronic F-68. The cell structures were as large as 3 mm in diameter but readily dissociated into single cells with minimal agitation. Viral infection inhibited aggregation for all cultivation conditions tested.

Viable cell concentrations were calculated using trypan blue exclusion and a hemocytometer. In addition to pH and glucose, samples of spent medium from the HARV and shaker flask were assayed for the presence of $O_2$, $CO_2$, lactate and ammonia. Both $O_2$ and $CO_2$ were measured with a Corning Model 601A Blood Gas Analyzer (Ciba Corning Diagnostics, Norwood, Md.). The YSI Model 27 Industrial Analyzer for glucose measurements was also used to enzymatically detect lactate (YSI kit 2329). Ammonia concentration was determined spectrophotometrically by monitoring the reductive amination of 2-oxoglutarate to glutamate in the presence of glutamate dehydrogenase (Sigma kit 171).

Sf9 cells cultured in the HARV exhibit a characteristic metabolism that is profoundly different from that of shaker cultures derived from the same cell line. To emphasize this difference, HARV cultures of Sf9 cells upon this metabolic transformation have been designated as RES cells in memory of Russell E. Schlorff, a former NASA attorney who worked on this patent application and has recently passed away.

FIG. 1 compares growth and viability profiles for HARV and shaker cultures. The lag phase was extended in the HARV by over 50 hours as RES cells adapted to the low-turbulence environment. After this time, doubling times in exponential phase were approximately the same in the two vessels, 40 to 45 hr. During lag and exponential phase, viability exceeded 90% in both vessels. Maximum cell density in the shaker flask surpassed that in the HARV by nearly 20% at $1.28 \times 10^7$ viable cells/ml; however, this concentration was maintained for only a limited period relative to the HARV. Twenty-four hours after the onset of stationary phase in shaker cultures, there was a noticeable reduction in cell viability from 92 to 82%. After an additional twenty hours, there was rapid cell death. For RES cultures in the HARV, stationary phase was extended for at least a week without any loss in viability or cell concentration.

As discussed above, these differences in culture performance become magnified when the HARV is compared to more turbulent bioreactors. Sparged stirred tanks and airlift bioreactors are used routinely for Sf9 cultivation. Murhammer, D. W. and Goochee, C. F., *Biotechnol. Prog.*, 6, 391 (1990) have reported maximum cell densities for these vessels that are substantially less than in the HARV, 1.5 to $4.0 \times 10^6$ total cells/ml. These values are on a total rather than a viable cell basis as reported for the HARV. Maximum viable cell densities would be even less. Similar values were reported by Ogonah, O., Shuler, M. L., and Granados, R. R., *Biotechnol. Lett.*, 13, 265 (1991).

During cultivation, the HARV provided sufficient $O_2/CO_2$ exchange for cell growth. Oxygen concentrations were comparable in the two vessels: 110 to 180 mm Hg in the shaker flask verses 93 to 170 mm Hg in the HARV (Table 1). Carbon dioxide concentration, however, was substantially lower in the HARV by a factor of 4 on average as a result of more efficient removal by the bioreactor or lower production by the cells. FIG. 2 reveals that shaker cultures required more medium replacement than HARV cultures, as much as a factor of two times more after 275 hr of culturing. Despite this greater exchange of medium, the shaker contained higher waste product concentrations for lactate and ammonia (Table 1). Lactate concentrations did not exceed 500 mg/l in the HARV but surpassed 850 mg/l in the shaker flask. Comparable results were obtained for ammonia—the shaker flask contained between 21–35 mg/l; the HARV, 21–28 mg/l. These differences in waste accumulation indicate that the low-turbulence environment of the HARV significantly affected cell metabolism.

TABLE 1

SUMMARY OF CULTIVATION CONDITIONS FOR HARV CULTURE OF RES CELLS AND SHAKER CULTURE OF Sf9 CELLS

| Parameter Measured | Unit | Value in HARV | Value in Shaker Flask |
|---|---|---|---|
| [Cell] | viable cell/ml | $1.0 \times 10^6$–$1.12 \times 10^7$ | $1.0 \times 10^6$–$1.28 \times 10^7$ |
| Viability | % | 92–98 | 34–97 |
| Reactor Volume | ml | 50 | 50 |
| Rotational Speed | rpm | 12–21 | 100 |
| [Dissolved $O_2$] | mm Hg | 93–170 | 110–180 |
| [Dissolved $CO_2$] | mmHg | 1.3–4.6 | 3.6–14.6 |
| pH | | 5.9–6.4 | 5.6*–6.4 |
| [Glucose] | mg/dl | 100–250 | 75*–250 |
| [Lactate] | mg/l | 18–482 | 18–892 |
| [Ammonia] | mg/l | 21–28 | 21–35 |

*Because of rapid nutrient consumption and waste production in shaker cultures during death phase, pH and glucose concentration fell below 5.9 and 100 mg/dl, respectively.

Glucose, pH, lactate and ammonia data are shown in FIGS. 3A, 3B, 3C and 3D respectively on a per cell basis so that intrinsic changes in metabolic activity can be easily discerned. For all four parameters measured, nutrient utilization and waste production differed dramatically in the two vessels. In the HARV, the rate of pH change and lactate production were less than in the shaker flask during lag and stationary phase, but approached the corresponding shaker parameters during exponential phase. The differences between the vessels were the greatest during the last 100 hr of cultivation. Here, the ratio of the shaker flask to HARV data exceeded a factor of 3 for pH change and 4 for lactate production.

Figure 3A:
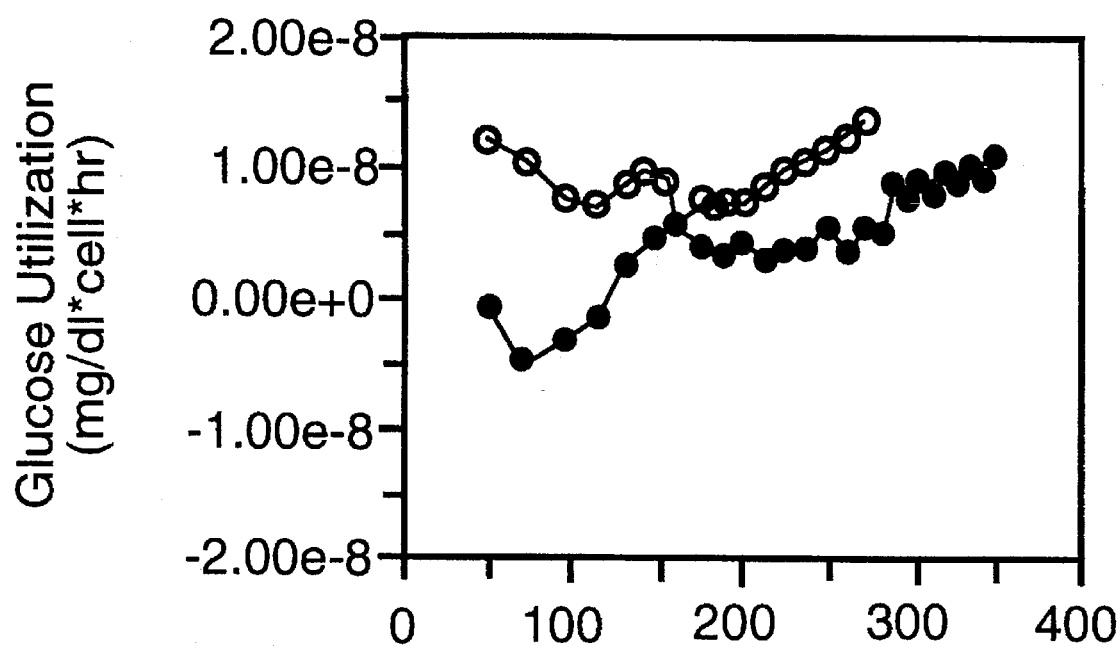
FIGS. 3A to 3D. Intrinsic metabolic activities of HARV culture of RES cells and shaker culture of Sf9 cells. Nomenclature for the two vessels is the same as in previous figures. Plotted are glucose utilization FIG. 3A, pH change FIG. 3B, lactate production FIG. 3C and ammonia production FIG. 3D.
Figure 3B:
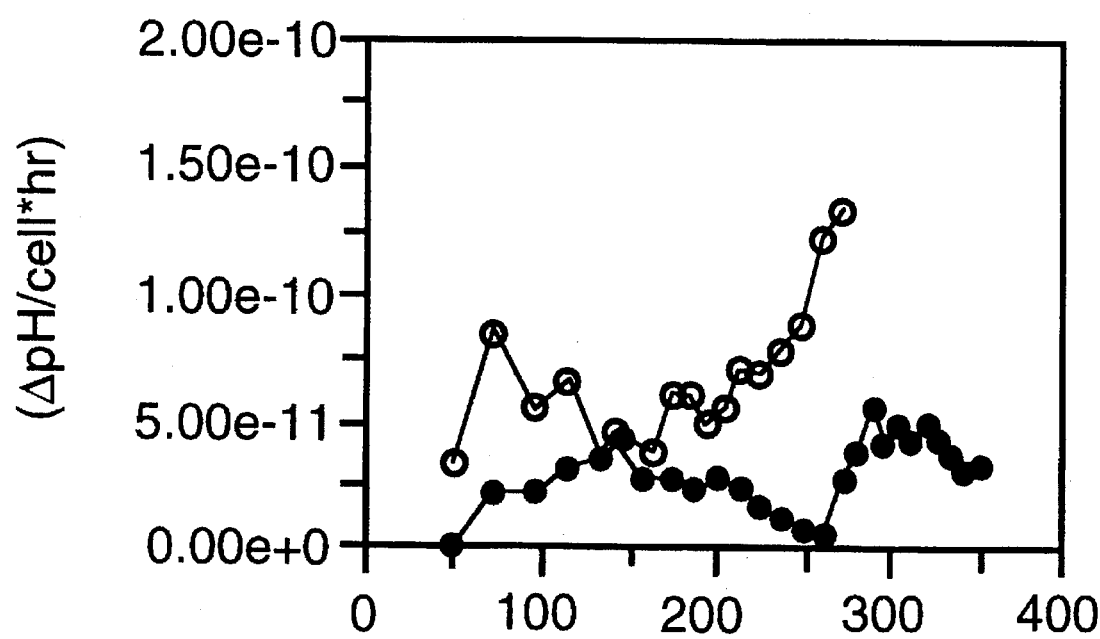
Figure 3C:
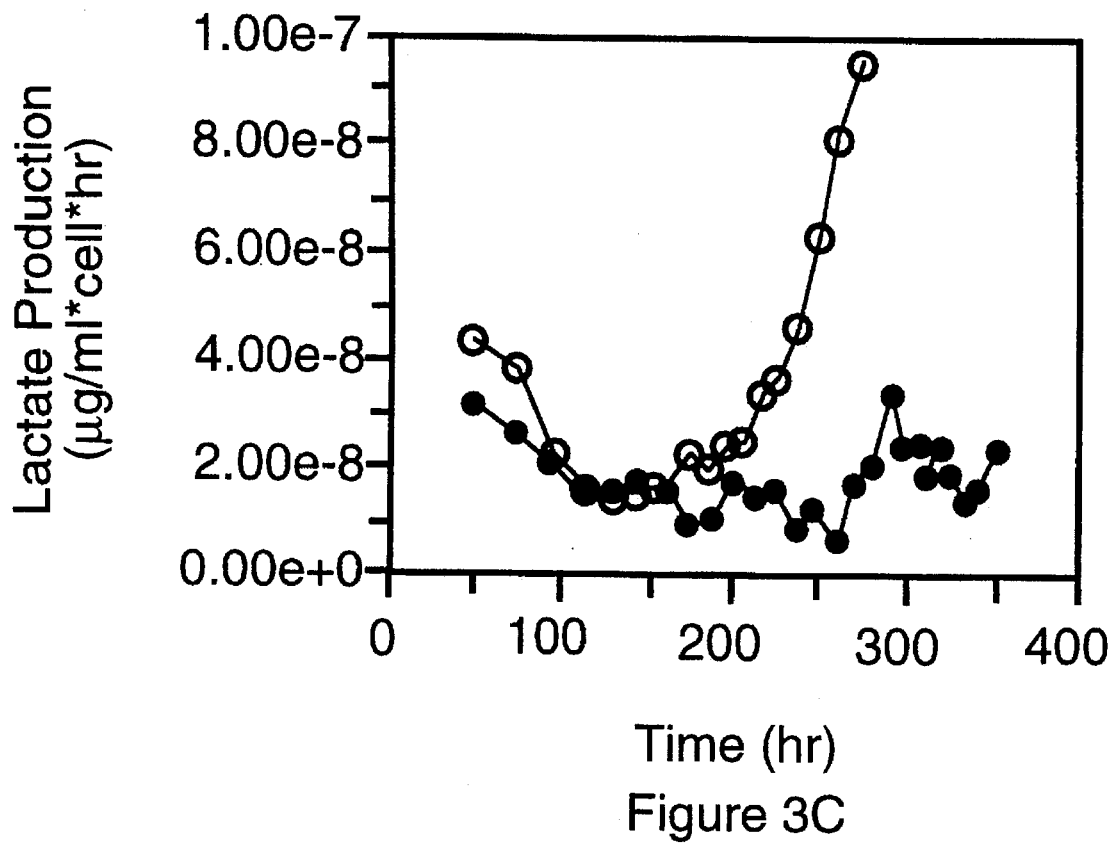
Figure 3D:
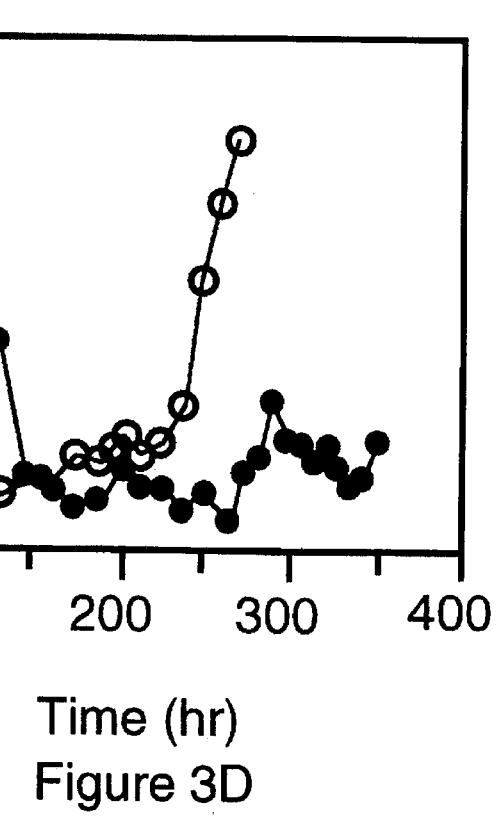

Glucose utilization and ammonia production followed a different trend (FIGS. 3A and 3D). In the shaker flask, glucose was consumed throughout cultivation. Not only was consumption less in the HARV, but glucose was produced during lag phase and the early part of exponential phase. The maximum rate of glucose production equaled $0.5 \times 10^{-8}$ mg/dl-cell-hr and occurred 75 hr after inoculation as RES cells entered exponential phase. When glucose was produced, ammonia production rose by a factor of two (FIG. 3 D). When glucose was subsequently consumed in the HARV after 150 hr of cultivation, ammonia production fell to values comparable to those in the shaker flask. Enhanced ammonia production during this period may reflect consumption of an alternate nutrient as an energy source, such as amino acids, which would liberate ammonia upon consumption [Kamen, A. A., Tom, R. L., Caron, A. W., Chavarie, C., Massie, B., and Archambault, J., *Biotechnol. Bioeng.*, 38, 619 (1991)]. Glucose production has been noted by Wang, M. Y., Kwong, S., and Bentley, W. E. *Biotechnol. Prog.*, 9, 355 (1993), but they did not speculate about its cause. Possibly, glucose accumulated in HARV cultures as RES cells consumed complex sugars such as maltose. Regardless of factors causing the metabolic transformation, the cellular processes exhibited unpredictable characteristics.

The metabolic data presented in FIG. 3 coupled with the medium replacement data in FIG. 2 indicate that the effects of HARV cultivation on cell metabolism were two fold. First, fewer nutrients were consumed by RES cells in the HARV during stationary phase. In additions, different metabolic pathways were utilized in the HARV as evidenced by glucose production and enhanced ammonia production in lag phase and as reflected in the yield coefficients for lactate and ammonia in stationary phase. From FIG. 3, the yields of moles lactate and ammonia produced per mole glucose consumed were greater than 5 for the shaker flask during the last 50 hr of cultivation, whereas these yields were less than 2.5 in the HARV during the same period. When hydrodynamic forces are minimized as in the HARV, the data presented suggest that metabolic energy is directed away from the repair of cellular damage to other cellular processes and that fewer nutrients are consumed by RES cells.

For viral infection, RES cells were exposed to a recombinant *Autograhpa californica* baculovirus from Invitrogen Corporation. Specifically, the HARV was seeded with Sf9 cells at a density of $0.7 \times 10^6$ viable cells/ml. The cultivation protocol was followed until the cells saw a normal doubling time (the cell density increased from $0.7 \times 10^6$ to $1.3 \times 10^6$ in approximately 24 hours), confirming the onset of exponential growth. The reactor was inoculated with virus at the onset of exponential growth in order to maximize virus yield. For the inoculation, 20% of the conditioned medium was removed and replaced with an equal volume of fresh medium containing the calculated amount of virus for an MOI (multiplicity of infection) of 10. Thereafter, the infected culture received a 10–20% medium change as needed to maintain the pH between 6.1 and 6.3 and the glucose concentration between 100 and 200 mg/dl. The cell density and viability were checked daily, as the baculovirus is pathogenic towards Sf9 cells, causing eventual cell death and lysing. When the number of viable cells dropped to 10% of the total cell number, a maximum virus yield was reached, and the experiment was terminated. This transforms the insect cell line to include a DNA sequence encoding for a selected polypeptide. In this case the baculovirus and β-gal were used as a model system. The model system was then cultured in a horizontally rotating vessel modulated to create low shear conditions which facilitated recombinant polypeptide production.

Infected cultures were maintained in the HARV and in spinner flasks for 180 hours after the initial inoculation. During this time, there were profound differences in the response of the insect cells to virus infection with these two types of bioreactor. Both the HARV and spinner-flask cultures were infected at a concentration of $1.3 \times 10^6$ viable cells/ml with a MOI of 10 as described above. The HARV culture grew for an unexpected period of 35 hours after infection to $1.7 \times 10^6$ viable cells/ml while retaining a viability that exceeded 90%. After this initial period of growth, both viability and cell concentration dropped until they reached 8.2% and $1.2 \times 10^5$ viable cells/ml, respectively, at the end of the experiment. In contrast, shaker cultures experienced a continuous reduction in viability and cell concentration throughout the experiment until these values reached 6.4% and $4.0 \times 10^4$ viable cells/mi. It was discovered that over the entire 180 hours of cultivation, viable cell concentration remained higher in the HARV by approximately a factor of 2 or greater. The improvement is attributed to the unexpected altered metabolism. Metabolism is focused on viral products and not diverted to the repair damage results from detrimental shear forces. These higher concentrations can result in a greater yield of baculovirus and recombinant proteins from the HARV culture.

After infection with baculovirus, RES cells in the HARV retain a distinctive metabolic profile that distinguish them from Sf9 cells. Glucose utilization and change in the pH of conditioned medium are examples of this behavior. The pH of both shaker and HARV cultures changed at approximately the same rate during the initial 24 hours of infection: $3.1 \times 10^{-9}$ ΔpH units/cell hr in shaker flasks and $2.5 \times 10^{-9}$ ΔpH units/cell hr in the HARV. For the remainder of the experiment in shaker flasks, pH changed at a slightly higher rate of $4.7 \times 10^{-9}$ ΔpH units/cell hr after 60 hours of infection and $6.0 \times 10^{-9}$ ΔpH units/cell hr after 180 hours. Rather than an increase, RES cultures in the HARV experience a decrease in the rate of pH change as infection progressed to $0.85 \times 10^{-9}$ ΔpH units/cell hr after 60 hours and $0.29 \times 10^{-9}$ ΔpH units/cell hr after 180 hours. There are analogous data for glucose. Glucose utilization in the HARV was less than in shaker flasks. In the HARV, the rate at which glucose was consumed was reduced from a value of $1.4 \times 10^{-7}$ mg/dl cell hr after 35 hours of infection to $0.67 \times 10^{-7}$ mg/dl cell hr after an additional 54 hours. For shaker flasks, the initial rate was higher at $7.7 \times 10^{-7}$ mg/dl cell hr after 35 hours. This rate also was lowered as the infection progressed but only to $2.0 \times 10^{-7}$ mg/dl cell hr.

To determine virus production as a function of time, infected cultures were titered daily using the following blue plaque assay from Invitrogen Corporation. Sf9 cells were seeded into four 60×15 mm animal cell culture plates at 80% confluency and allowed to attach for 30 to 45 minutes. The conditioned medium was removed from the attached cells after rocking the plates from side to side to pick up dead cells and debris. Each plate was washed with 1 ml fresh medium to remove any remaining debris, being careful not to pipet across the cell layer as this would have dislodged the attached cells.

Ten-fold dilutions of the virus inoculum were prepared. For the first dilution ($10^{-1}$), 0.11 ml of cell-free virus sample was added to 0.99 ml of fresh medium. For the second dilution ($10^{-2}$), 0.11 ml of the first dilution was added to 0.99 ml fresh medium. This process was continued for subsequent dilutions through $10^{-8}$.

The virus dilutions were added to the prepared plates. One milliliter of a dilution was uniformly spread on each plate, making four plates, one each of $10^{-8}$, $10^{-7}$, $10^{-6}$, and $10^{-5}$ dilutions. The virus was allowed to infect the cells for one hour. After one hour, the virus inoculum was drawn off, leaving the attached, infected cells on the plate.

The agarose was prepared during the hour in which the virus was infecting the cells. For four plates, 0.38 g agarose was added to 12.5 ml Millipore water and autoclaved at 120° C. for 15 minutes. Once autoclaved, the agarose was maintained at 40° C. The 2X Hink's TNM-FH Medium (containing fetal bovine serum to compensate for the toxicity of the agarose, Gibco BRL Life Technologies, Gaithersburg, Md.) was warmed to 40° C. Three milligrams of X-gal (Sigma) were mixed with 0.15 ml DMSO. To the warmed agarose, 0.125 ml of the X-gal-DMSO mixture and 12.5 ml of the 2X medium were added. Each plate received 5 ml of the agarose mixture, being careful not to dislodge the attached cells by pipetting across the cell layer. Once the agarose had solidified, the plates were stored in a plastic bag with a damp paper towel to create a humid environment to prevent cracking of the agarose.

By the tenth day, blue recombinant plaques were visible. The virus titer was determined by taking the number of plaques on a plate and dividing by the dilution factor of that plate.

β-Galactosidase (β-Gal) served as a model protein to investigate recombinant protein production from baculovirus-infected insect cells in the HARV and baculovirus served as a model virus for pathogen production. This protein is frequently used in Sf9 studies since it is readily available and can be easily assayed. A mutant form of the baculovirus *A. californica* (or a pathogen type in an alternate embodiment for virus production) containing the gene coding for β-Gal was used as a cloning vector to introduce and express the β-Gal gene in Sf9 cells. As the virus replicates, the β-Gal gene is expressed along with native viral proteins. The effect that the HARV has on recombinant β-Gal production is two fold; it enhances both total and intrinsic production. Because the HARV cultures insect cells to larger cell densities than other conventional bioreactors, the overall production of the HARV culture on a per volume basis is larger than in conventional systems. On an intrinsic level, the HARV also raises the rate of recombinant protein synthesis through viral infectivity and/or cell metabolism. As for the former, the low-turbulence environment of the HARV facilitates adherence of viral particle to the cell surface. As for the latter, the changes that the HARV causes in cell metabolism may result in an increase in gene transcription, protein translation, post-translational processes and protein secretion from the cell.

The level of intracellular and extracellular recombinant β-galactosidase expression was measured with a spectrophotometric assay on a Thermomax microplate reader. The process for collecting the recombinantly produced polypeptide included pipetting spent cell culture media from the culture vessel into a test tube. The contents of the test tube were then assayed for the amount of β-gal present in the spent media. In an alternate embodiment, spent cell culture media with suspended cells was pipetted into a test tube. The test tube was centrifuged at 500×g to pellet cells containing recombinantly produced polypeptide. The supernatant was removed and the cells were lysated by standard sonication or detergent preparations. The lysate was suspended in buffer and assayed for recombinantly produced polypeptide, for example β-gal. In an alternate embodiment the spent cell culture media containing recombinantly produced polypeptide or the lysate containing recombinantly produced polypeptide can be purified by standard molecular weight exclusion filtration, by column chromatography, by immunoprecipitation/absorption, or by centrifugation techniques known in the art for the specific recombinantly produced polypeptide. Specifically, the assay determined the amount of β-gal present based on the enzymatic conversion of o-nitrophenyl-β-D-galactopyranoSide (ONPG, Sigma) to o-nitrophenol and galactose. It measured the steady-state rate of ONPG consumption at 410 nm, 37° C., and pH 7.3 in 250 μl of solution of 0.08M $NAPO_4$, 0.11 M 2-mercaptoethanol, 0.001M $MgCl_2$—$6H_2O$, and 0.002M ONPG and 8 μl of enzymatic β-gal sample. At a wavelength of 410 nm, the molar extinction coefficient for ONPG is 3.5 mole $cm^{-1}$. Doubling the amount of β-gal present did not affect measurements of rate per unit amount of enzyme.

In the HARV, β-gal began to accumulate intracellularly 35 hours after the initial infection. Extracellular expression of the recombinant protein began 12 hours later. Using the infection protocol described above, the maximum β-gal concentration achieved in the HARV was 29 U/ml medium intracellularly and 7 U/ml extracellularly after 105 and 140 hours of infection, respectively. By definition, a unit of β-gal hydrolyzes 1.0 μmole/min ONPG at pH 7.3 and 37° C. The maximum yield of β-gal (i.e., the combination of its intracellular and extracellular concentration) was 33 U/ml also at 105 hours. From 105 to 180 hours when the experiment was terminated, the β-gal yield dropped to 9 U/ml possibly as the result of denaturation or proteolytic activity. For comparison, the maximum intracellular and extracellular concentrations of μ-gal in shaker cultures infected under identical conditions were 3.7 U/ml at 95 hours and 3.2 U/ml at 155 hours, respectively. The maximum yield occurred at 95 hours and was 5 U/ml. As in the HARV, the yield dropped to 4.3 U/ml as the experiment progressed to 180 hours. During the course of the experiment it was discovered that the yield of β-gal was greater in the HARV by a factor ranging between 2 to 7.

Recombinant baculovirus containing a foreign gene encoding a desired polypeptide can be generated using a modified procedure of Summers, M. D. and Smith, G. E., *A Manual of Methods for Baculovirus Vectors and Insect Cell Culture Procedures, Texas Agricultural Experiment Station Bulletin No.* 1555 (Texas A&M University, College Station, Tex., 1988). First, wild-type DNA would be purified from intact baculovirus particles with a cesium chloride/ethidium bromide gradient. Next, the foreign gene of interest would be cloned into pBlueBac (Invitrogen) or another baculovirus transfer vector. Sf9 cells would be co-transfected with both the recombinant transfer vector and purified wild-type viral DNA using a modification of the calciumphosphate precipitation technique. The infected cells would produce a combination of wild-type and recombinant virus progeny which generate white and blue plaques, respectively, upon titering the virus as described previously in this section. The recombinant baculovirus could be readily isolated from the plaques and amplified in Sf9 cells to the generate large quantities of intact virus.

In addition to viral infection, the HARV can be used to produce recombinant polypeptides from insect cells by stable transformation. Specifically, stably-transformed Sf9 cell lines that continuously express recombinant B-gal and recombinant tissue plasminogen activator are available from Texas A.& M University. These cell lines could be cultured in the HARV using the preferred process described above in this section for non-infected Sf9 cells. Because the nutrient requirements of the non-infected and stably-transformed Sf9 cells are very similar, we would expect that this similarity extend to their growth and metabolic profiles in the HARV. Thus, cultivation times for the stably-transformed cells should be greatly extended in the HARV because of the prolonged stationary phase. Since these cells continuously produce recombinant polypeptides, the HARV should significantly increase production times and product yields over that achieved in a shaker flask or other conventional bioreactors. Moreover, the HARV should reduce the cost of production, since we have demonstrated for non-infected Sf9 cells that medium requirements are less in the HARV than in shaker flasks.

Stably transformed Sf9 cells containing a foreign gene encoding a desired polypeptide can be created with a number of different plasmids [jarvis, D. L., Fleming J.—A. G. W., Kovacs, G. R., Summers, M. D., and Guarino, L. A., *Biotechnology*, 8, 950 (1990); Helgen, J. C. and Fallon, A. M., *In Vitro Cell. Dev. Biol.*, 26, 731 (1990)]. One of these is recombinant pUC8 (Sigma) containing the IE1 promoter and IE1 coding region from the baculovirus *A. californica*. The foreign gene of interest or a neomycin resistance gene would be inserted into the IE1 coding region just downstream of the IE1 promoter. As described by Jarvis, D. L., Fleming J.-A. G. W., Kovacs, G. R., Summers, M. D., and Guarino, L. A., *Biotechnology*, 8, 950 (1990), Sf9 cells would be co-transfection with a modification of the calcium phosphate precipitation technique [Summers, M. D. and Smith, G. E., *A Manual of Methods for Baculovirus Vectors and Insect Cell Culture Procedures, Texas Agricultural Experiment Station Bulletin No.* 1555 (Texas A&M University, College Station, Tex., 1988)] using a mixture of two plasmids: one containing the neomycin resistance gene and the other containing the foreign gene of interest. Then, the cells would be cultivated in the presence of neomycin antibiotic (Gibco BRL Life Technologies). The Cells that grew under these conditions would contain the plasmid with the neomycin resistance gene. Individual colonies of cells from this transfected subset would be isolated and assayed for continuous expression of the foreign gene of interest. Those colonies that assayed positive would be the desired stably transformed Sf9 cells.

The disclosure herein will be understood by those skilled in the art. It is not intended to limit the claimed invention to those processes and products expressly discussed. Alternative methods to practice this invention will be recognized by those skilled in the art.

We claim:

1. A process for producing a selected polypeptide in insect cells comprising the steps of
   (a) obtaining insect cells;
   (b) stably transforming the insect cells to include a selected DNA Sequence encoding a selected polypeptide; and
   (c) culturing the stably transformed insect cells in a rotating culture vessel completely filled with culture medium wherein said medium is oxygenated and low shear conditions are maintained wherein the hydrodynamic force is less than 0.5 dyne/cm$^2$ during which time the insect cells produce the selected polypeptide, and wherein, while cultured in a rotating culture vessel, the stably transformed insect cells grow as single cells and have the following characteristics: (i) prolonged stationary phase, (ii) altered metabolic profile, wherein the amount of utilised glucose is reduced, wherein the amount of lactate produced is reduced and wherein the amount of ammonia produced is reduced, (iii) reduced waste product production, and (iv) reduced nutrient consumption.

2. The process of claim 1 further comprising an additional step (d) of collecting the selected polypeptide.

3. The process of claim i further comprising an additional step of purifying the selected polypeptide.

4. The process of claim 1 wherein the selected DNA sequence in step (b) further includes a DNA sequence encoding a promoter which specifically promotes the expression of the selected DNA sequence.

5. The process of claim i wherein an additional step before genetic transformation in step (b) comprises culturing the insect cells in a rotating culture vessel completely filled with culture medium wherein said medium is oxygenated and low shear conditions are maintained wherein the hydrodynamic force is less than 0.5 dyne/cm$^2$, wherein, while cultured in a rotating culture vessel, the stably transformed insect cells grow as single cells.

6. The process of claim 1 wherein the transformation of the insect cells in step (b) comprises utilizing baculovirus containing the selected DNA sequence.

7. The process of claim 1 wherein the insect cells in step (a) are Lepidopteran cells.

8. A process for producing a selected polypeptide in insect cells comprising the steps of
   (a) obtaining insect cells;
   (b) culturing the insect cells in a rotating culture vessel completely filled with culture medium wherein said medium is oxygenated and low shear conditions are maintained wherein the hydrodynamic force is less than 0.5 dyne/cm$^2$ during which time the insect cells produce the selected polypspride, and wherein, while cultured in a rotating culture vessel, the stably transformed insect cells grow as single cells and have the following characteristics: (i) prolonged stationary phase, (ii) altered metabolic profile, wherein the amount of utilized glucose is reduced, wherein the amount of lactate produced is reduced and wherein the amount of ammonia produced is reduced, (iii) reduced waste product production, and (iv) reduced nutrient consumption;
   (c) inserting a DNA sequence encoding a selected polypeptide into a pathogenic insect virus;
   (d) inoculating the insect cell culture of step (b) with sufficient amounts of the pathogenic virus of step (c) to infect the insect cells;
   (e) culturing the infected insect cells of step (d) for a period of time sufficient to produce the selected polypeptide encoded by the DNA Sequence; and
   (f) collecting the selected polypeptide.

9. The process of claim 8 further comprising the additional step of purifying the polypeptide collected in step (f).

10. The process of claim 8 wherein said insect cells are Lepidopteran cells.

11. The process of claim 8 wherein the pathogenic insect virus is a baculovirus.

* * * * *